US009254385B2

(12) United States Patent
Greenberg et al.

(10) Patent No.: US 9,254,385 B2
(45) Date of Patent: Feb. 9, 2016

(54) VISUAL PROSTHESIS FOR PHOSPHENE SHAPE CONTROL

(75) Inventors: Robert Greenberg, Los Angeles, CA (US); Mark Humayan, Glendale, CA (US); Devyani Nanduri, Los Angeles, CA (US); Matthew McMahon, Washington, DC (US); James Weiland, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 795 days.

(21) Appl. No.: 12/466,303

(22) Filed: May 14, 2009

(65) Prior Publication Data

US 2009/0287276 A1   Nov. 19, 2009

Related U.S. Application Data

(60) Provisional application No. 61/127,714, filed on May 14, 2008.

(51) Int. Cl.
*A61N 1/36* (2006.01)
*A61N 1/05* (2006.01)

(52) U.S. Cl.
CPC .......... *A61N 1/36046* (2013.01); *A61N 1/0543* (2013.01)

(58) Field of Classification Search
CPC .................... A61N 1/36046; A61N 1/0543
USPC ...................................... 607/53–54
See application file for complete search history.

(56) References Cited

U.S. PATENT DOCUMENTS

| 5,109,844 | A | 5/1992 | de Juan, Jr. et al. | |
| 5,935,155 | A | 8/1999 | Humayun et al. | |
| 6,400,989 | B1 | 6/2002 | Eckmiller | |
| 6,442,431 | B1 * | 8/2002 | Veraart et al. | 607/54 |
| 6,458,157 | B1 | 10/2002 | Suaning | |
| 6,507,758 | B1 * | 1/2003 | Greenberg et al. | 607/54 |
| 7,079,900 | B2 * | 7/2006 | Greenburg et al. | 607/54 |
| 2004/0172092 | A1 | 9/2004 | Greenberg et al. | |
| 2004/0172098 | A1 | 9/2004 | Greenberg et al. | |
| 2006/0058857 | A1 * | 3/2006 | Tano et al. | 607/54 |
| 2007/0244523 | A1 * | 10/2007 | Grill et al. | 607/54 |

OTHER PUBLICATIONS

R.E. Marc, B.W. Jones, C.B. Watt. E. Strettoi. Neural remodeling in retinal degeneration. Progress in Retinal and Eye Research. 22: 607-655. 2003.

C. Gargini, E. Terzibasi, F. Mazzoni, E. Strettoi. Retinal organization in the retinal degeneration 10 (rd10) mutant mouse: a morphological and ERG study. The Journal of Comparative Neurology. 500: 222-238 (2007).

(Continued)

*Primary Examiner* — Alyssa M Alter
(74) *Attorney, Agent, or Firm* — Scott B. Dunbar

(57) ABSTRACT

The present invention is an improved method of stimulating visual neurons to create artificial vision. It has been found that varying current of visual stimulation can create varying percept brightness, varying percept size, and varying percept shape. By determining the attributes of predetermined current levels, and using those attributes to program a video processor, more accurate video preproduction can be obtained.
The present invention also includes an electrode array having alternating large and small electrodes in rows at a 45 degree angle to horizontal in the visual field.

9 Claims, 7 Drawing Sheets

(56) References Cited

OTHER PUBLICATIONS

E. Margalit, M. Mauricio, J.D. Weiland, R.J. Greenberg, G.Y Fujii, G. Torres, D.V. Piyathaisere, T.M. O'Hearn, W. Liu, G. Lazzi, G. Dagnelie, D.A. Scribner, E de Juan, M.S. Humayun. Retinal Prosthesis for the Blind. Survey of Ophthalmology. 47(4): 335-356. 2002.
M. Mahadevappa, J.D. Weiland, D. Yanai, I. Fine, R.J. Greenberg, M.S. Humayun. Perceptual thresholds and electrode impedance in three retinal prosthesis subjects. IEEE Transactions in Neural Systems Rehabilitation Engineering. 13(2):201-6. 2005.
M. S. Humayun, E. de Juan, J. D. Weiland, G. Dagnelie, S. Katona, R.J. Greenberg and S. Suzuki. Pattern electrical stimulation of the human retina. Vision Research. 39: 2569-2576. 1999.
M.K. Hu. Visual Pattern Recognition by Moment Invariants. IRE Transactions of Information Theory. 179-187. 1962.
C. de balthasar, S. Patel, A. Roy, R. Freda, S. Greenwald, A. Horsager, M. Mahadevappa, D. Yanai, M.J. McMahon, M.S. Humayun, R.J. Greenberg, J.D. Weiland, I. Fine. Factors affecting perceptual thresholds in epiretinal prostheses. Investigative Opthalmology and Visual Science. 49(6):2303-14. 2008.

* cited by examiner

VISUAL PROSTHESIS FOR PHOSPHENE SHAPE CONTROL

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for neural stimulation.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

U.S. Pat. No. 5,575,813, Edell describes a cantilever approach to attaching an electrode array to a retina. Edell describes a fundamentally flat array attached at one end acting as a cantilever. This applied uneven forces on the retina. It will apply greater force closer to the tack and greater force along the edges of the array.

SUMMARY OF THE INVENTION

The present invention is an improved method of stimulating visual neurons to create artificial vision. It has been found that varying current of visual stimulation is can create varying percept brightness, varying percept size, and varying percept shape. By determining the attributes of predetermine currently levels, and using those attributes to program a video processor, more accurate video preproduction can be obtained.

The present invention also includes an electrode array having alternating large and small electrodes in rows at a 45 degree angle to horizontal in the visual field.

A Retinal Prosthesis system to restore sight for the blind is under development. The system is analogous to cochlear implants, in which photoreceptor input is bypassed and replaced by direct electrical stimulation of the retinal ganglion cells. Currently, six test subjects have been implanted with a 4×4 electrode array and stimulator. We report here psychophysical clinical data examining how stimulation amplitude affects phosphene shape and repeatability on a single electrode. Phosphene shape data was quantified by a set of numerical descriptors calculated from image moments. Comparison of phosphene descriptors for a single electrode across repeated trials and amplitudes levels measured the repeatability within an amplitude group. Our experimental findings show that stimulation of the retina creates repeatable percept shapes and that an increase in stimulation amplitude causes a significant change in size and shape of phosphenes.

Image shape is better controlled without interfering electrical fields. Alternating electrode sizes in a checkerboard pattern provide no adjacent electrical fields of the same shape and size. This reduces interference between adjacent electrical fields.

It is difficult to implant an electrode array in a perfectly level location. Accurate image shape requires correction of image rotation by physical or electronic means. The correction may be based upon array observation, patient feedback or both.

Further embodiments are shown in the specification, drawings and claims of the present application.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Retinal prosthesis systems elicit percepts by directly stimulating the inner retina, bypassing the functionality of the outer-retinal photoreceptors. The electrode array 10 is implanted in the macular region of the retina. Electrical signals are transmitted to the device through a neural stimulator 14. flex circuit cable 12 serves to connect the stimulator 14 with the epiretinal electrode array 10. Stimulation patterns are generated by either direct specification from a PC, or through a real-time head-mounted video camera capture and processing system. The PC/camera information is transmitted wirelessly to the stimulator vai tuned coils 16 and 17. An image of the array located with respect to the fovea is shown in FIG. 1.

Previous clinical experiments have focused on temporal-spatial characteristics of percepts in terms of threshold and brightness. A better understanding of spatial integration with multi electrode stimulation will improve the devices form perception capabilities. Exploring multi-electrode spatial integration first requires a thorough understanding of single electrode percepts, characterized by the properties of shape, color, size, location, and brightness. Here we explore how stimulation amplitude affects phosphene shape and repeatability.

Figure 1A:
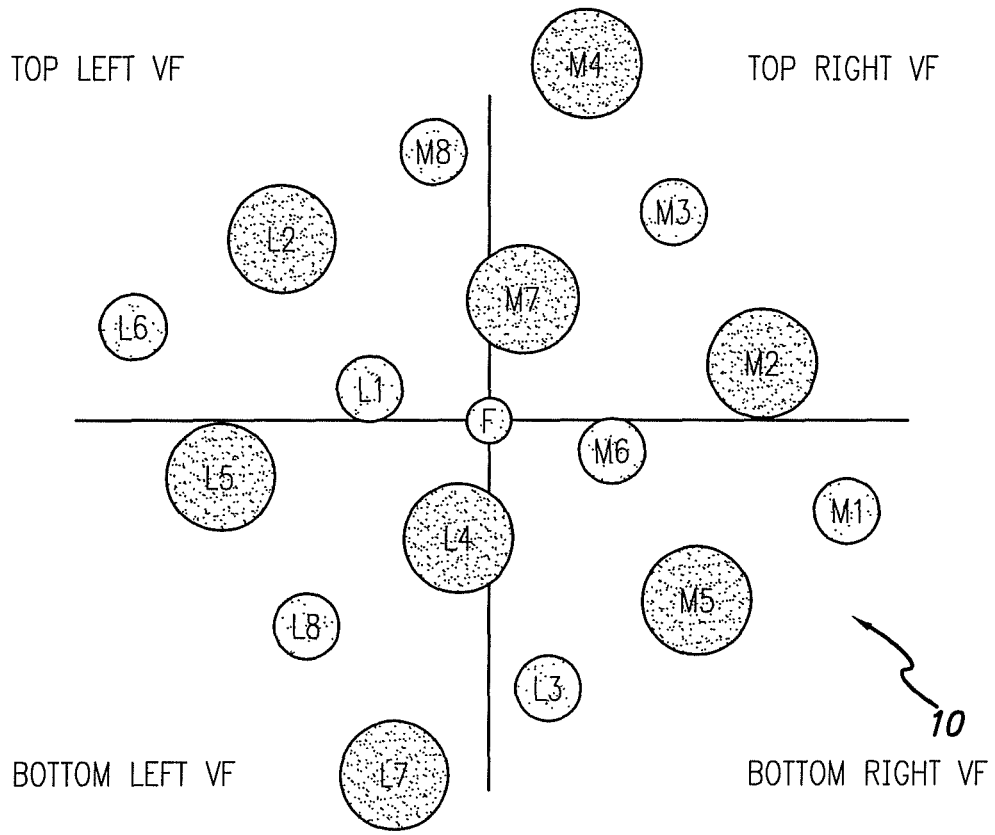
FIG. 1a is schematic view of a checkerboard patterned electrode array.
Figure 1B:
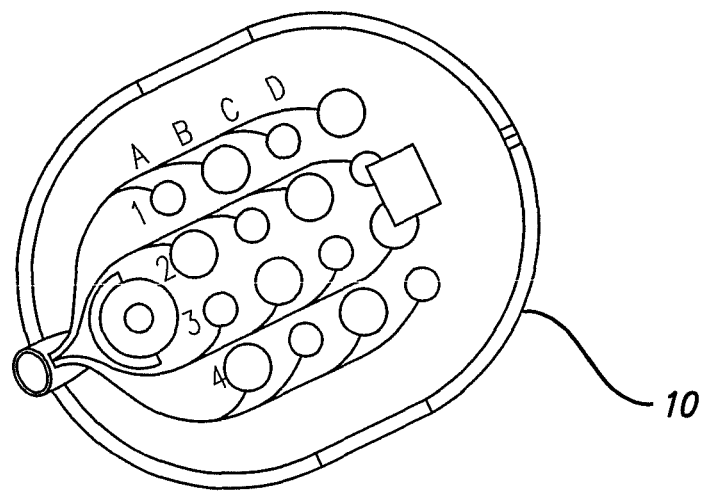
FIG. 1b is a perspective view of a checkerboard pattern electrode array.

Referring to FIGS. 1a and 1b, it is advantageous to provide electrodes in varying size. Different sized electrodes produce different sized electrical fields, and therefore, are less likely to interfere with the electrode field of the neighboring electrode. In the preferred embodiment, the electrodes are provided in a checkerboard pattern of electrode sizes so no two adjacent electrodes have the same size. In the preferred embodiment, two electrode sizes are used, one that is 250 mm diameter electrodes 4 and the other 500 mm diameter electrodes 2, as shown in FIG. 1. The smaller electrode 4 produces a smaller electric field which makes it interfere less with the larger field of the larger electrode 2.

It is also advantageous to center the array over the fovea in the topological plane of the retina in at least two directions (for instance in the directions corresponding to vertical and horizontal visual fields). The retina approximates a partial sphere. An installed array approximates a smaller partial sphere adjacent to the retina (either subretinal or epiretinal). The two parallel topological planes (array and retina) are optimally arranged with the topological center of the array directly over the fovea.

FIG. 1 also shows an electrode array at an angle. With current surgical techniques, it is difficult to implant an electrode array with a precise desired rotation. Hence, the system must be capable of correcting for any rotation in the array placement. The correction may be electronic or physical (rotating the camera). While software rotation gives more precise control, it requires correction of each frame. Physical rotation of the camera need only be done once. Hence a decision of electronic versus physical correction will be based on available processing power. Further, it is advantageous to have the array physically rotated, preferably 45 degrees, to avoid multiple electrode falling along the same axion. Multiple electrode along the same axion may tend to interfere with the signals of each other.

Determining the correct rotation may be accomplished by observation, patient feedback or both. In the preferred embodiment, observation of the array is used first, follow by patient feed back to fine tune the correction. Using the observation method, a fundus photo is taken of the fundus and the array. The angle of the array is measured on the photograph and the camera is set to a complementary angle. The patient feed back method involves the patient looking at a known vertical and/or horizontal line. The patient may direct or clinician or directly move the camera until the known line appears correct. Alternatively, the patient can use an input device, such as a joystick to adjust a known line for electronic correction. The preferred procedure is as follows.

4. Procedure 4.1 Rotation

This procedure is necessary to compensate for any rotation of the implanted electrode array in a subject. The first important step is to determine the angle of the array on the subject's retina. This step will be performed by the Research team. Retinal photographs will be analyzed for each subject and a summary table (and accompanying graphics) will document the rotation angle for each subject. If the rotation angle is less than 5 degrees, do not perform any camera rotation. There are a number of sources of imprecision that justify our decision not to compensate for small rotations. For example, there are small variations in tilt of the head during retinal photography, there is variability of the position of the glasses on the subject's, and we have limited precision in our ability to adjust the camera position in the lenses. In addition, the visual system can easily re-calibrate for small rotations and shifts of the retinal image.

The procedure is an iterative one, where the experimenter measures the camera angle, adjusts it if it is incorrect, and re-measures the new position.

We start with the angle measured from the fundus photo.

Measuring the camera rotation angle:

1) Turn on the system in communication mode, start CFS, and click on the Video tab.
2) Have the subject sit in a chair and look straight ahead.
3) Hold the camera angle target (camera angle target.pdf) 6 to 8 inches in front of the subject and view the sub-sampled image of the target in the Camera Output window. Without rotating the target (keep it perfectly straight), translate the target in from of the subject and determine which guide line is horizontal in the Camera Output window. Estimate the angle to the closest 5 degrees.

Modifying the rotation angle:

1) Remove all hot glue from the lenses and the camera.
2) Place the camera in the guide hole and secure it in place with a piece of HandiTak.
3) Rotate the camera to the desired rotation angle and keep it held in place with the HandiTak.

4.2 Alignment

Once the camera angle is correct, the experimenter needs to align the camera with the projected position of the electrode array in the visual field when the subject is looking straight ahead.

The procedure is an iterative one, where the experimenter measures the camera alignment, adjusts it if it is incorrect, and re-measures the new alignment.

Measuring the camera alignment:

1) Turn on the system in communication mode, start CFS, and click on the Video tab.
2) Have the subject sit in a chair and look straight ahead.
3) Hold the small white square target (Target 3B) at arm's length in front of the subject and view the image of the target in the Camera Output window. Translate the target in from of the subject until the white square is centered in the Camera Output window.
4) Turn on stimulation for approximately 0.5 seconds by clicking the button that controls stimulation.
5) Ask the subject to point to the location of the phosphene on the board.
6) The position they point to is the alignment location of the camera. If they do not point to the square then adjust the camera to move the camera in that direction, relative to the square.

Adjusting the camera alignment:

1) Tilt the camera within the hole to adjust it's position. If the subject pointed down and to the left of the square, then move the camera in this direction. Be careful not to modify the rotation angle of the camera, which was previously adjusted.
2) Make sure that the camera maintains it's position with the HandiTak.

4.3 Fixing the Camera in Place

1) Place a small spot of hot glue on each side of the camera to affix it to the lenses.
2) Remove the HandiTak form the camera and frame The correction process is further described in US patent application 2004/0172098 for Pixel Re-Mapping for Visual Prosthesis which is incorporated herein by reference.

Shape Similarity with Image Moments

Quantitative shape comparison requires characterizing images by a set of numerical image descriptors. Upon definition, images are compared on the similarities and differences of their descriptor values. Image moments are a basic set of descriptors calculated from weighted averages of the pixel intensities across an image. Global features of the image shape, such as size, orientation and form can be extracted from image moments.

Geometric moments are the simplest to calculate and for a binary image I(x,y), with dimensions M by N, moments are given by the equation:

$$M_{ij} = \sum_{i=1}^{M} \sum_{j=1}^{N} x^i y^j I(x, y) \tag{1}$$

In a binary image, geometric moments can be used to calculate the scale (total mass) of the image and the center of mass using the $M_{00}$, $M_{10}$ and $M_{01}$ moments. The center of mass is given by the equation $$\bar{x} = \frac{M_{10}}{M_{00}}, \bar{y} = \frac{M_{01}}{M_{00}} \tag{2}$$

Centralized moments shift the geometric moment equation by the center of mass to correct for translational differences. The definition of a centralized moment is:

$$\mu_{ij} = \sum_{i=1}^{M} \sum_{j=1}^{N} (x - \bar{x})^i (y - \bar{y})^j I(x, y) \tag{3}$$

Major and Minor axes, along with orientation of the shape can be calculated from the centralized moments. These features are invariant to translational effects.

There are several ways to extract global shape features invariant to translation, rotation and scale. The mathematical foundation for a set of moments invariant to translation, rotation and scale was first proposed by Hu in 1962. The seven Hu moment feature descriptors are extremely applicable to shape recognition. Each moment is derived from linear and non linear combinations of normalized central moments up to the order three. Here we compare phosphene shapes to one another using scale information extracted from geometric moments, orientation calculated from centralized moments and Hu moment descriptors.

Methods

Experimental Setup

Stimulation patterns were directly specified on the PC and coded by a custom-built video processing unit as a serial data stream. The information was relayed to the implant via the wireless link. After each stimulus presentation, the head mounted camera recorded the subject tracing the phosphene data on a grid screen with a tracking tipped pen to a digital video recorder (DVR). Head movement was minimized with a chin rest. Frame of reference was maintained by using the head mounted camera, instead of an external camera. Video files were analyzed off-line to extract phosphene shape data from the frame to frame tracking of the pen tip. In the first part of the tracking software, the grid screen background was used to set the coordinate system to match the appropriate field of view. Subsequently, the pen tip was detected in HSV color space and the location recorded for each frame of the video file. Lastly, a binary shape data file was built with pen tip coordinate locations for all frames. Binary files for all stimulations were compared using shape analysis techniques.

Stimulation Parameters

The stimulation study protocol was approved by the University of Southern California IRB. Percept shape data was collected on 4 electrodes with a single subject. First, threshold was measured for a biphasic 500 ms, 20 Hz pulse train with a pulse width 0.45 ms. Perceptual threshold was determined as the current amplitude needed to detect the stimulus on 50% of trials, corrected for false alarms using a 3up-1down staircase with interleaved catch trials. Using previously obtained threshold data, shape data was then collected for five repeat measurements at amplitude values of 30 uA, 100 uA and 200 uA greater than threshold (all other stimulus parameters held constant). Electrode-amplitude repeats were randomized with the three remaining electrode stimulations.

Shape Analysis

Each binary image was analyzed by breaking down the image into its moment descriptors. Shape data was compared using image moment analysis. The size of each shape was obtained from $0^{th}$ geometric moment. The orientation, major and minor axes were calculated from the eigenvalues and eigenvectors of the centralized moments. Hu moments were used to compare shape features invariant to translation, rotation and scale. Similarity between two shapes with seven vector Hu moments p and q was obtained by calculating the Euclidean distance between moments given by the equation:

$$ED = \sqrt{\sum_{i=1}^{7}(p_i - q_i)^2} \quad (4)$$

A large Euclidean distance value implied shapes were different, while a small ED value indicated shape similarity.

Results

Shape data was analyzed in four separate ways. Firstly, data within an electrode-amplitude set, trials were established to be repeatable. Subsequently, the effects of stimulation amplitude on phosphene shape were explored across four different electrodes. Shape was evaluated for size, orientation and invariant Hu moments.

Repeatability

Figure 2:
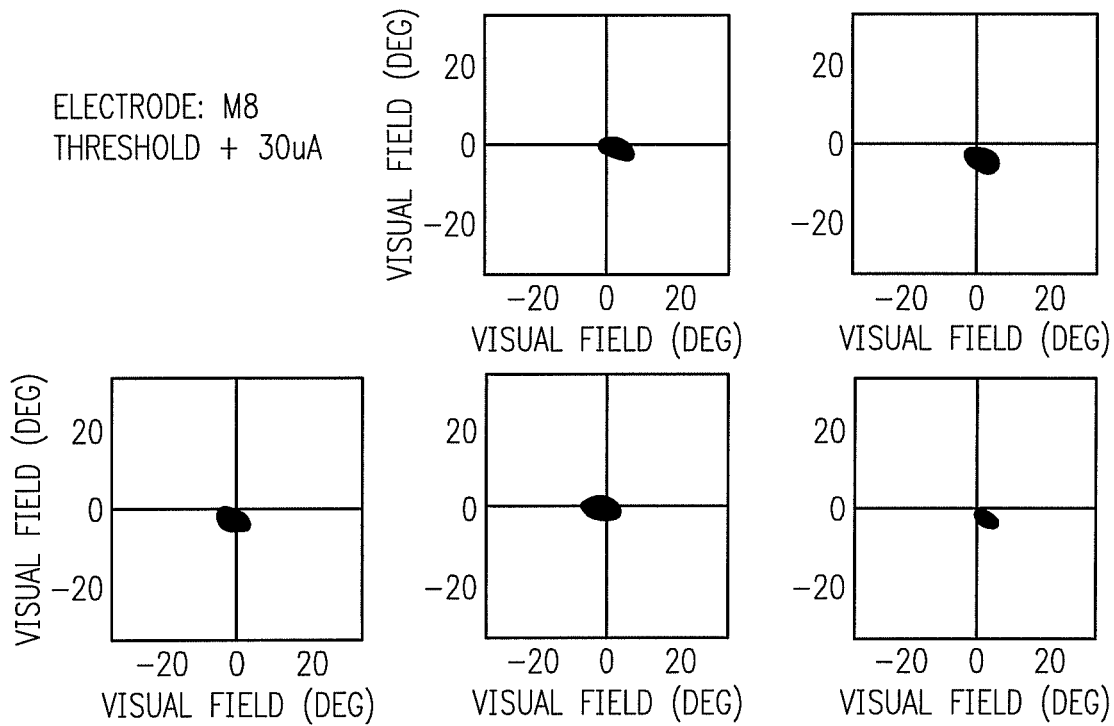
FIG. 2 shows binary images for electrode M8 amplitudes threshold+30 uA, repeats not significantly different from each other ($p > 0.05$).
Figure 3:
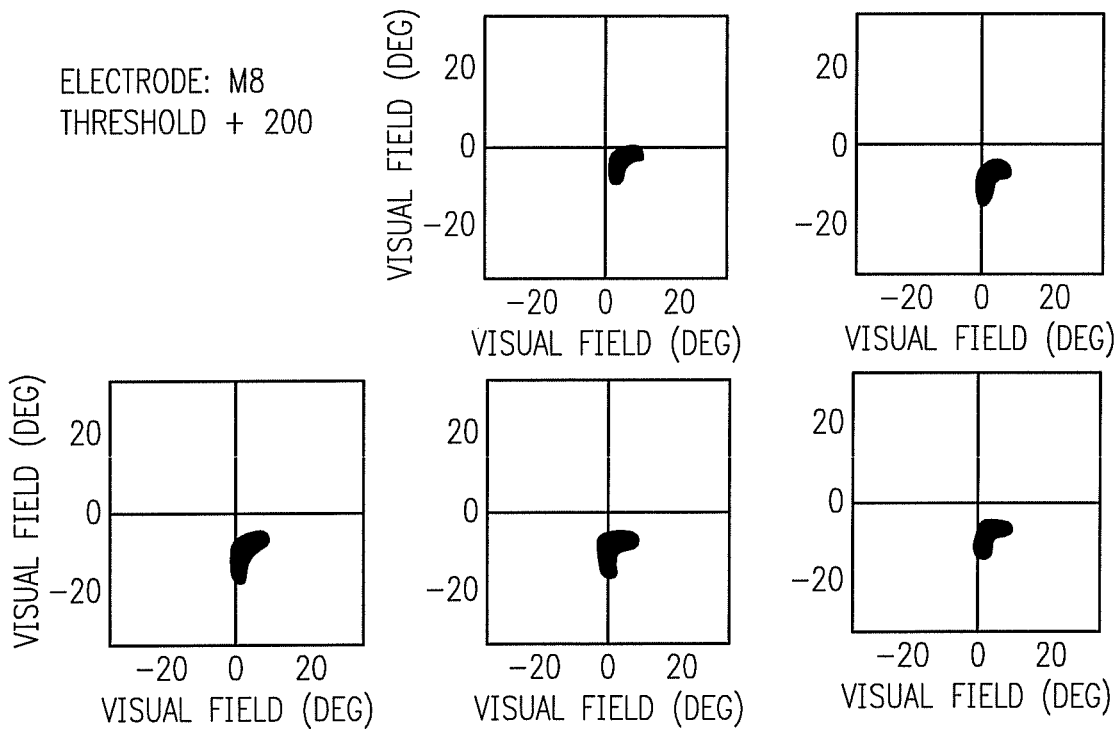
FIG. 3 shows binary images for electrode M8 amplitudes threshold+30 uA, repeats not significantly different from each other ($p > 0.05$).

Shape data repeatability was established for a single electrode at the three amplitude levels. For each amplitude level, a t-test was used to calculate repeatability across the five repeated measurements. All t-tests within an electrode-amplitude group indicated that there was no significant difference between the mean Hu moment of four repeats compared to a fifth repeat (p>0.05). An example of shape data of five repeats collected for stimulation of electrode M8 at amplitude 30 uA above threshold is shown in FIG. 2. Shapes appear to be similar across repeats matching results of significance t-test. Shapes are again repeatable for electrode M8 at an amplitude threshold+200 uA as shown in FIG. 3, but different to shapes shown in FIG. 1, obtained at 30 uA greater than threshold.

Scale

Figure 4:
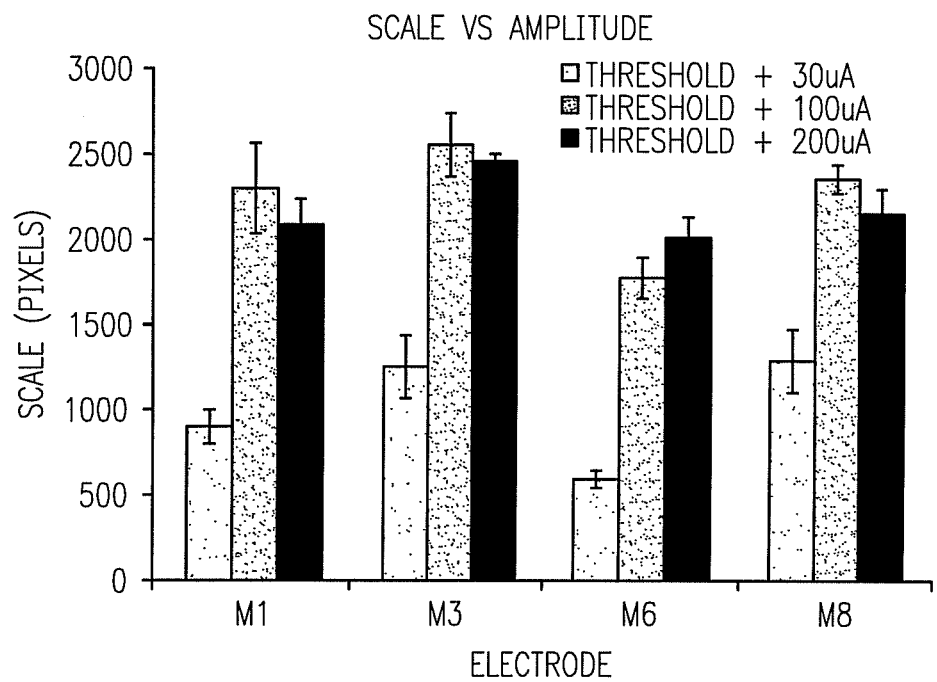
FIG. 4 shows mean size of percept for different amplitude levels across four electrodes.

The size of the phosphenes was calculated by measuring pixel area of the shapes. A larger percept was indicated by a greater number of dark pixels. The average number of pixels was calculated with standard error for repeated trial measurements across the four electrodes and three different amplitudes sets. The results are plotted below in FIG. 4.

The size of the percept appears to increase with amplitude between 30 uA greater than threshold to 100 uA greater than threshold. Based on the standard error bars, there does not appear to be any discernible difference in size of percept between phosphenes obtained with stimulation 100 uA above threshold to 200 uA above threshold consistently across all 4 electrodes. This would indicate that increases in phosphene size reaches a limit, beyond which size may stay relatively constant. This threshold of constant size may be useful in fitting (i.e. one might pick currents over a certain value to use so that the received image would be size invariant.

Orientation

Figure 5:
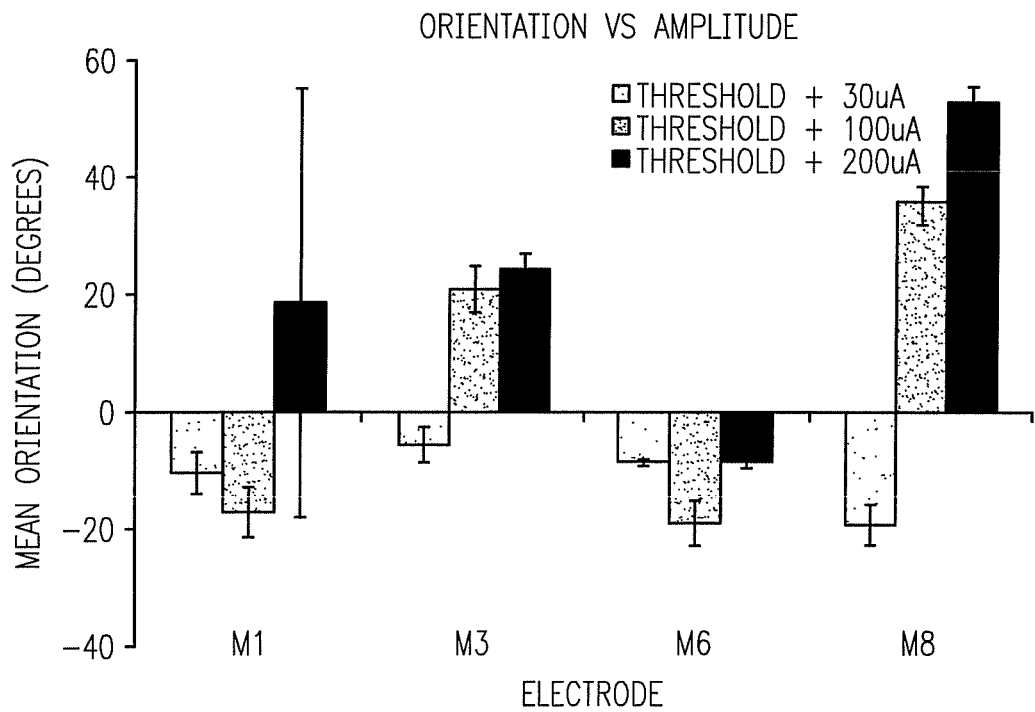
FIG. 5 shows mean orientation of phosphenes for 30, 100, 200 uA above threshold across four single electrodes.

The change in orientation with amplitude was calculated using centralized moments of the binary image. The mean shape orientation indicates the angle of the major axis from the horizontal. There does not seem to be any differentiable trend between phosphene orientation and increasing amplitudes. Hu moment comparison likely is a better indicator of shape changes. The results are plotted in FIG. 5.

Hu Moments

Figure 6:
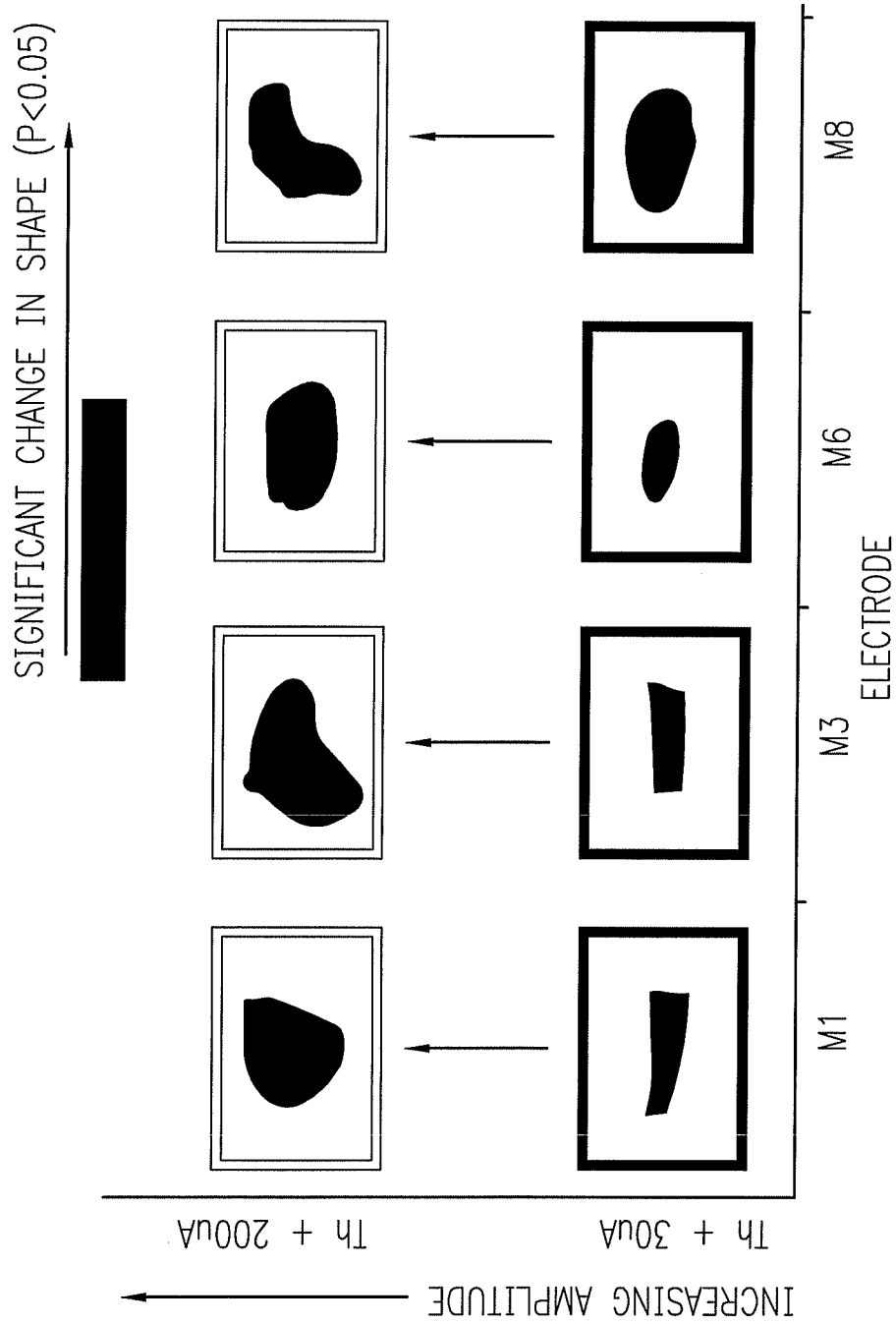
FIG. 6 shows shape changes with increasing amplitude were significant ($p < 0.05$).

The mean Hu moments and standard deviation were calculated from the five repeated trials for an electrode-amplitude group. For each electrode, paired t-tests were conducted between mean Hu moments of all three amplitude levels by calculating the Euclidean distance between Hu moments. T-tests indicated that there was a significant change in Hu moments between 30 uA above threshold and 200 uA above threshold groups for all 4 electrodes. Results of different shape groupings are shown in FIG. 6. The best representative shape from the five repeated trials is shown for each amplitude level.

DISCUSSION AND CONCLUSION

Electrically elicited phosphenes change in shape and size with increasing amplitude. Experiment repeatability relies on subjects ability to draw percepts accurately and consistent between trials. Blind subjects do not have visual feedback on the shapes drawn and will vary in drawing ability more than a sighted subject.

Results indicate that quantitative shape analysis of phosphenes provides a method to evaluate the change of single electrode percept shapes with varying stimulation parameters. This valuable shape information provides insight into the underlying neural mechanisms of stimulation and will move towards a predictive multi-electrode model of percepts generated.

One novel finding is that amplitude, pulse width or frequency can be selected to control phosphene shape and size, thus providing more accurate resolution. Thus, specific ranges of parameters, such as amplitude, might be optimum to produce more regular phosphenes across the array.

Figure 7:
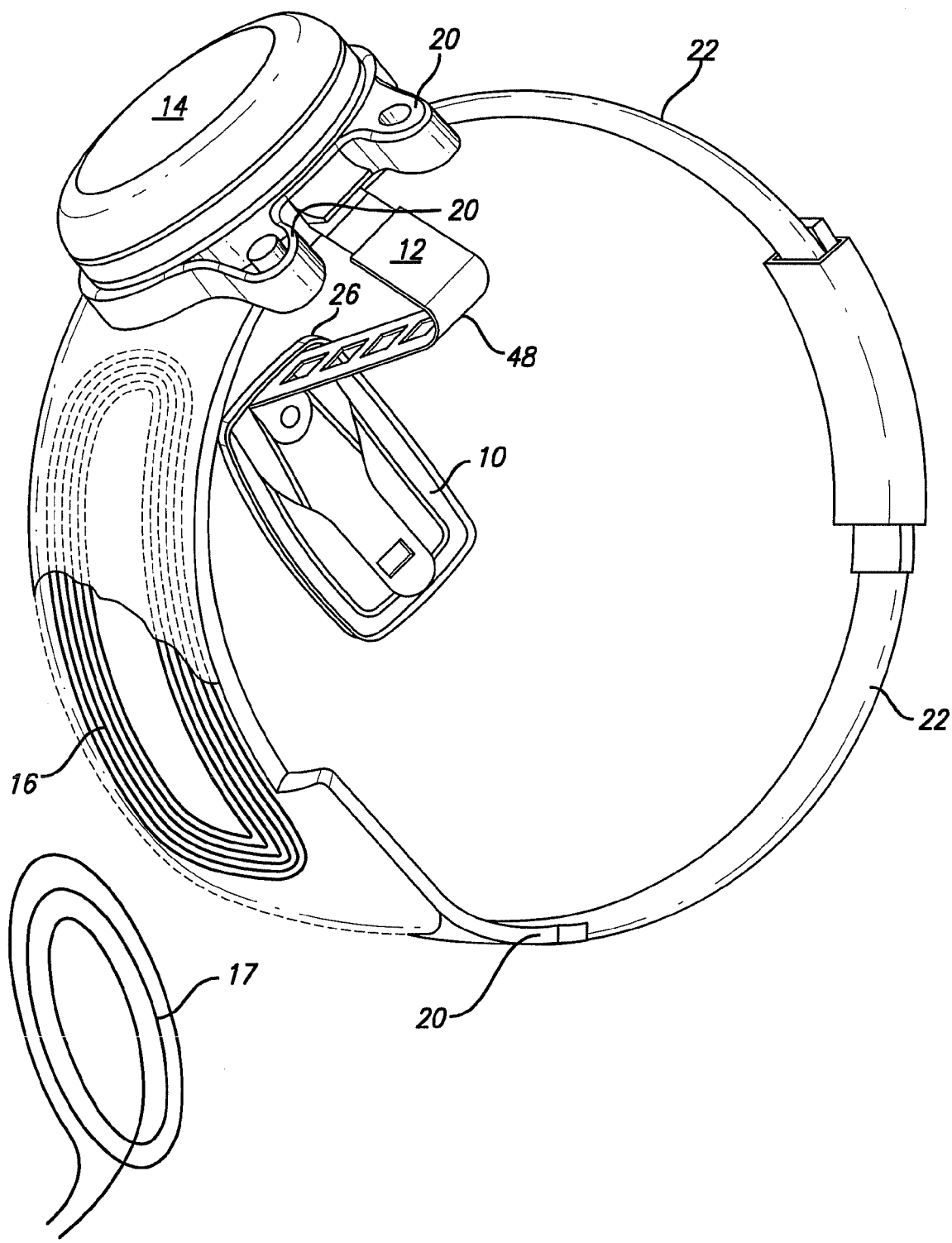
FIG. 7 is a perspective view of the implanted portion of the preferred retinal prosthesis.

FIG. 7 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 8:
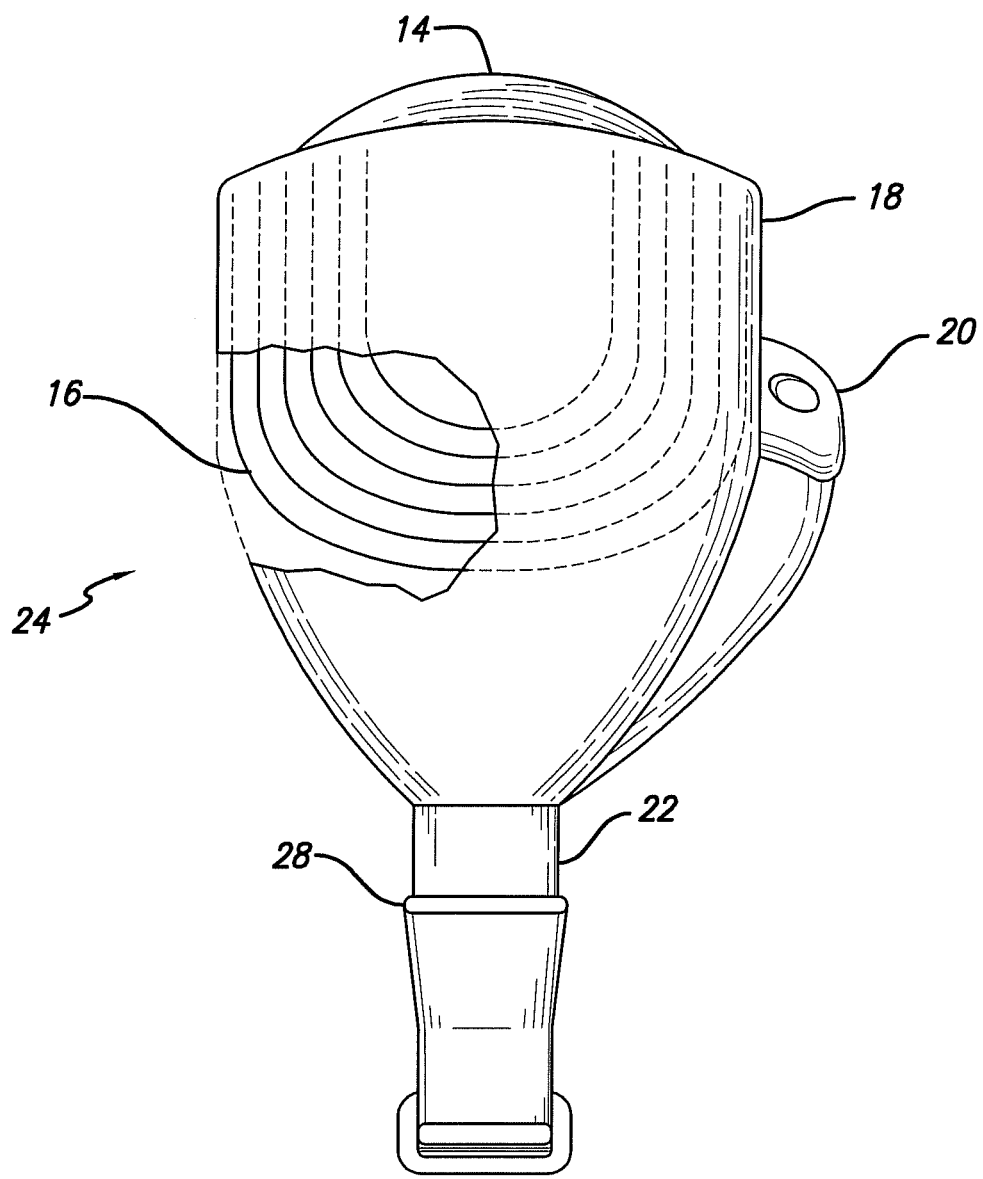
FIG. 8 is a side view of the implanted portion of the preferred retinal prosthesis showing the fan tail in more detail.

FIG. 8 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 9:
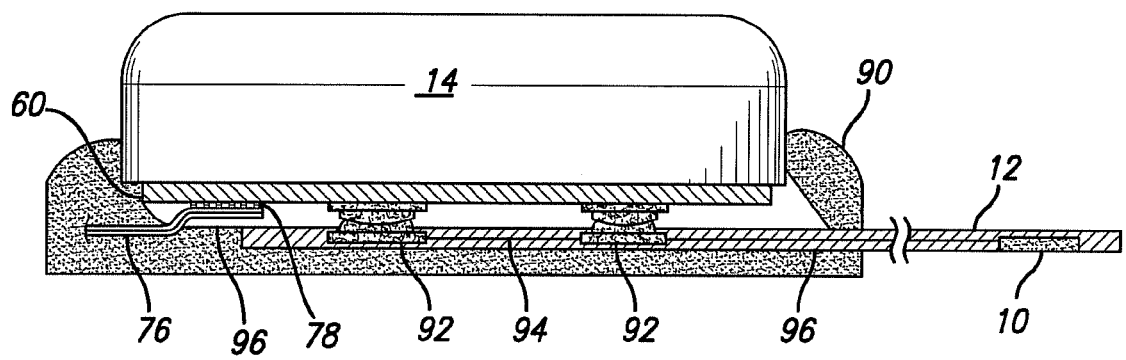
FIG. 9 is a view of the completed package attached to an electrode array.

Referring to FIG. 9, the flexible circuit 1, includes platinum conductors 94 insulated from each other and the external environment by a biocompatible dielectric polymer 96, preferably polyimide. One end of the array contains exposed electrode sites that are placed in close proximity to the retinal surface 10. The other end contains bond pads 92 that permit electrical connection to the electronics package 14. The electronic package 14 is attached to the flexible circuit 1 using a flip-chip bumping process, and epoxy underfilled. In the flip-chip bumping process, bumps containing conductive adhesive placed on bond pads 92 and bumps containing conductive adhesive placed on the electronic package 14 are aligned and melted to build a conductive connection between the bond pads 92 and the electronic package 14. Leads 76 for the secondary inductive coil 16 are attached to gold pads 78 on the ceramic substrate 60 using thermal compression bonding, and are then covered in epoxy. The electrode array cable 12 is laser welded to the assembly junction and underfilled with epoxy. The junction of the secondary inductive coil 16, array 1, and electronic package 14 are encapsulated with a silicone overmold 90 that connects them together mechanically. When assembled, the hermetic electronics package 14 sits about 3 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 14 and the secondary inductive coil 16 on the lateral side of the sclera, the electronics package 14 is mounted higher than, but not covering, the secondary inductive coil 16. In other words the thickness of the secondary inductive coil 16 and electronics package should not be cumulative.

It is also advantageous to place protective material between the implant device and the conjunctiva. This is particularly important at the scleratomy, where the thin film electrode array cable 12 penetrates the sclera. The thin film electrode array cable 12 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX® (ePTFE), TUTOPLAST® (sterilized sclera), MERSILENE® (polyester) or silicone.

Figure 10:
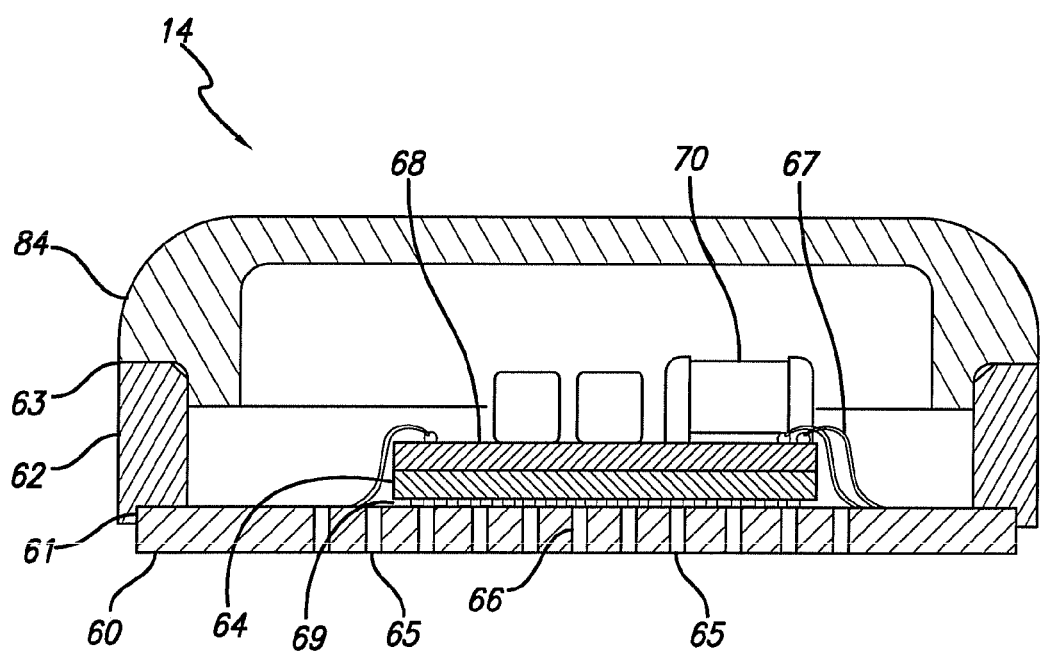
FIG. 10 is a cross-section of the package.

Referring to FIG. 10, the package 14 contains a ceramic substrate 60, with metalized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64 a ceramic hybrid substrate 68 is positioned. On the ceramic hybrid substrate 68 passives 70 are placed. Wirebonds 67 are leading from the ceramic substrate 60 to the ceramic hybrid substrate 68. A metal lid 84 is connected to the metal case wall 62 by laser welded joint 63 whereby the package 14 is sealed.

Accordingly, what has been shown is an improved method making a neural electrode array and improved method of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of inducing the perception of an image comprising:
   providing a neural stimulator including a plurality of electrodes suitable to stimulate visual neural tissue;
   providing a plurality of stimulation signals at varying current levels on said plurality of electrodes;
   determining a subject's perception of shape of percept for each of said plurality of stimulation signals on each of said plurality of electrodes;
   storing data for the subject's perception of shape of the percept for each of said plurality of stimulations signals on each of said plurality of electrodes; and
   stimulating the subject's visual neural tissue based on a source image and one of said plurality of stimulation signals selected from said stored data by selecting the stimulation signals and electrodes that most closely match the source image.

2. The method according to claim 1, where said plurality of stimulation signals vary in current.

3. The method according to claim 1, wherein said plurality of stimulation signals vary in total charge.

4. The method according to claim 1, wherein selecting the stimulation signals is selecting the stimulation signals with a minimum size percept.

5. The method according to claim 1, further comprising stimulating the visual neural tissue based on said source image and a subset of said plurality of stimulation signals wherein a size of percept is invariant.

6. A method of inducing the perception of an image comprising:
   providing a neural stimulator including a plurality of electrodes suitable to stimulate visual neural tissue;
   providing a plurality of stimulation signals at varying current levels on each of said plurality of electrodes;
   recording a subject's perception of a percept shape for each of said plurality of stimulation signals on each of said plurality of electrodes; and
   stimulating neural tissue based on comparing a source image with said recorded subjects perception of a percept shape for each of said plurality of percept signals on each individual electrode and selecting the stimulation signal with a recorded precept shape most closely matching the source image.

7. The method according to claim 6, where said step of recording is recording precept shapes and stimulation signals in a look up table.

8. The method according to claim 7, further comprising comparing said percept shapes with said image and stimulating visual neural tissue with a stimulation signal associated with the precept shape that most closely corresponds to said image.

9. The method according to claim 6, further comprising stimulating neural tissue based on said source image and a subset of said plurality of stimulation signals wherein the shape of percept is invariant.

\* \* \* \* \*